United States Patent [19]

Troy et al.

[11] Patent Number: 5,220,915
[45] Date of Patent: Jun. 22, 1993

[54] AIR DELIVERY AND CIRCULATION MEANS FOR A SURGICAL DRAPE

[75] Inventors: Thomas S. Troy; Lynn G. Dunford, both of Garden City, Kans.

[73] Assignee: Easy Breathe, Inc., Garden City, Kans.

[21] Appl. No.: 790,536

[22] Filed: Nov. 12, 1991

[51] Int. Cl.⁵ .................................... A61M 16/00
[52] U.S. Cl. .......................... 128/204.25; 128/200.24; 128/204.18; 128/205.26
[58] Field of Search ............ 128/204.18, 204.25, 128/205.26, 200.24, 202.27

[56] References Cited

U.S. PATENT DOCUMENTS

| | | | |
|---|---|---|---|
| 1,257,332 | 2/1918 | Erlandson | 128/200.24 X |
| 1,553,098 | 9/1925 | Napier | 128/200.24 X |
| 2,290,437 | 7/1942 | Kilgore | 128/200.24 X |
| 2,628,803 | 2/1953 | Krewson | 128/200.24 X |
| 3,403,677 | 10/1968 | Struve | 128/200.24 X |
| 3,482,571 | 12/1969 | Behrendt | 128/200.24 X |
| 3,859,993 | 1/1975 | Bitner | 128/205.26 X |
| 4,223,669 | 9/1980 | Morledge | 128/205.26 X |
| 4,321,917 | 3/1982 | Campbell | 128/205.26 |
| 4,377,161 | 3/1983 | Whitt | 128/200.24 |
| 4,508,117 | 4/1985 | Rodari | 128/204.21 |

FOREIGN PATENT DOCUMENTS

| | | | |
|---|---|---|---|
| 356547 | 9/1931 | United Kingdom | 128/204.25 |
| 718080 | 11/1954 | United Kingdom | 128/204.25 |

Primary Examiner—Edgar S. Burr
Assistant Examiner—Eric P. Raciti
Attorney, Agent, or Firm—Edward L. Brown, Jr.

[57] ABSTRACT

An air delivery and ventilation system for head surgery which is used under a drape including a flexible air supply conduit with discharge at inlet ends, the discharge end being elevated over the chest of the patient by a positioning bracket formed of bendable thin-gauge metal shaped with a pair of legs joined by a circular saddle which engages the discharge end, the pair of legs each being bendable around the opposite shoulder of the patient and inserted thereunder, a plug positioned in the remotely-located inlet end of the supply conduit having a small diameter oxygen passage with a nozzle on the end thereof positioned in the center of the plug along the axis of the conduit with the passage connected to a source of pressurized oxygen to produce a high velocity jet in the supply conduit, the plug further including air passage means surrounding the oxygen passage so as to provide substantial volumes of atmospheric air drawn into the conduit by the venturi action of the high velocity jet to provide low velocity oxygen-enhanced air from the discharge end of the supply conduit.

5 Claims, 1 Drawing Sheet

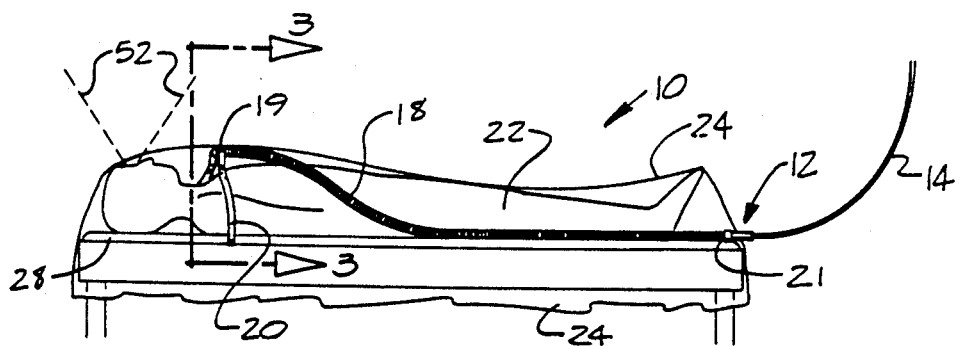
FIG 1
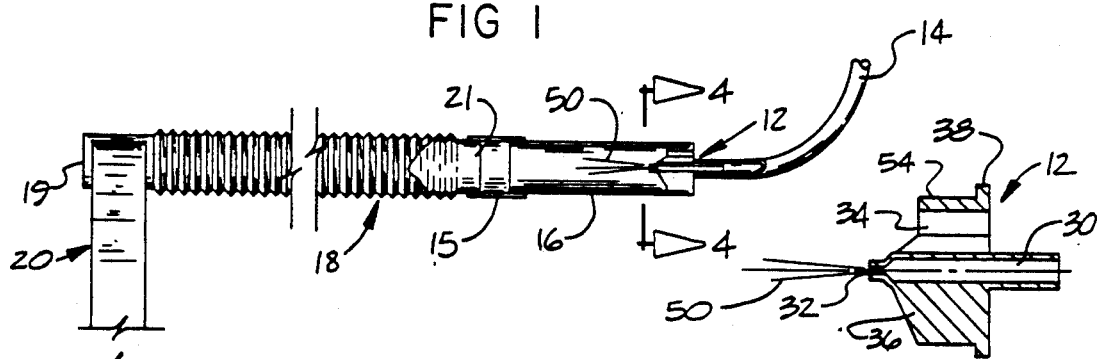
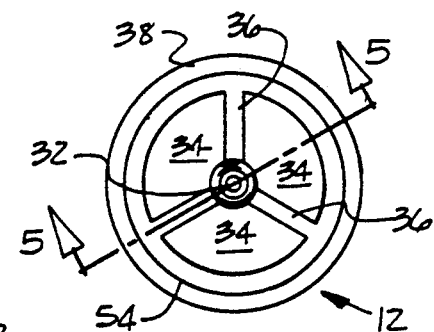
FIG 5
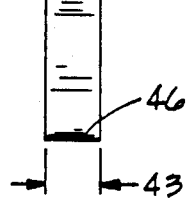
FIG 2
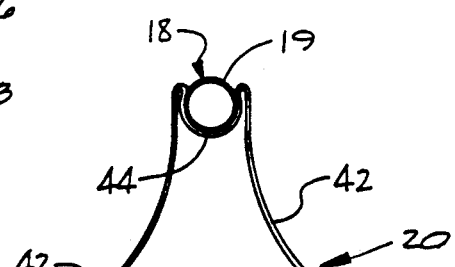
FIG 4
FIG 3

5,220,915

AIR DELIVERY AND CIRCULATION MEANS FOR A SURGICAL DRAPE

BACKGROUND OF THE INVENTION

The invention relates to a ventilation system for head and neck surgery used under a surgical drape so as to prevent the patient from rebreathing carbon dioxide. Excessive amounts of $CO_2$ in the blood leads to a condition known as hypercapnia. This is a universal problem with all draped head or neck surgeries performed under a local anesthetic. In patients who develop hypercapnia, significant medical problems can arise, such as elevated blood pressure, an increased sensitivity of the heart that can lead to arrhythmia, acute anxiety, claustrophobia, and disorientation.

Providing a surgical drape with support apparatus around the head, along with the provision of pressurized oxygen, is shown in U.S. Pat. Nos. 4,223,669 (Morledge) and 3,482,571 (Behrendt), both of which elevate the surgical drape above the patient's face. Additional U.S. Pat. Nos. 4,377,161 (Whitt) and 4,739,753 (Brehm) also teach surgical drape supports and oxygen breathing apparatus approximate the patient's face. In none of the patents previously mentioned is there a venturi action by the use of a high velocity jet within a conduit utilized to draw in additional outside air which is mixed with the high velocity jet and supplied in the area of the patient's face. Also, none of the above mentioned references teach a positioning bracket for the air supply conduit which is bendably positioned around the chest area of the patient as done in the present invention.

Another method commonly used to supply oxygen to patients under a drape is the utilization of a cannula which is inserted directly into the nasal passageway of the patient and provides a pressurized oxygen source directly into the patient's nasal passage. The cannula method does not provide a passage of a breeze of air over the patient's face which not only diminishes the $CO_2$ levels but also inhibits the claustrophobic feeling a patient sometimes has with a drape in contact with their face.

The general principle of utilizing a high pressure jet in a duct to draw in and pump surrounding stationary air is generally disclosed in U.S. Pat. No. 4,274,406 (Bartholomew) which is a tracheotomy mask. The high velocity jet in this mask configuration is offset from the axis of the inlet duct since it passes through the wall of the duct and the jet is not positioned along the axis of the duct for optimum performance.

U.S. Pat. No. 4,495,946 (Lemer) is a similar venturi action jet utilized for artificial respiration of a patient which is intermittently valved open and closed. The high speed jet in this patent is likewise offset from the center axis of the duct.

SUMMARY OF THE INVENTION

In accordance with the present invention, the air delivery system is utilized for a condition known as hypercapnia which is the presence of excessive concentrations of carbon dioxide in the blood. The system of the present invention supplies large volumes of oxygen-enhanced air to dilute the high concentration of carbon dioxide without using pure oxygen as taught in many of the above mentioned patents. The high velocity jet exiting the nozzle produces a lower pressure area causing the surrounding air in the duct to be drawn into the high velocity jet in a mixing action transmitting velocity to the entire air mass in the duct. The volume of gas exiting the duct is approximately 10 times the volume of $O_2$ entering the oxygen passage. The particular positioning of the oxygen passage and nozzle for the high velocity jet along the axis of the supply conduit provides an optimum venturi action. The positioning bracket of the present invention is a unique structure to any of the cantilevered or other design brackets shown in the above mentioned patents and provides lateral as well as longitudinal stability once in position for maintaining the discharge end of the air supply conduit over the patient's chest while partially lifting the surgical drape from the patient's face.

Therefore, the principal object of the present invention is to provide a new and improved air delivery and ventilation system to alleviate hypercapnia in head and neck draped surgeries and provide a breeeze of air across the patient's face.

Another object of the present invention is to provide a new and improved high velocity jet mixing means.

A further object of the present invention is to provide a new and improved positioning bracket for the discharge end of the air supply conduit which is readily adjustable in height and positioning around the shoulders of the patient.

BRIEF DESCRIPTION OF THE DRAWINGS

FIG. 1 is a pictorial illustration of a patient utilizing the air-delivery and ventilation system of the present invention under a surgical drape;

FIG. 2 is a side elevational view of the air supply conduit and mixing means in partial section and the positioning bracket with portions of the supply conduit and the positioning bracket broken away;

FIG. 3 is is a lateral section taken along lines 3—3 of FIG. 1;

FIG. 4 is a left end view of the injector plug to an enlarged scale taken along line 4—4 of FIG. 2; and FIG. 5 is a sectional view of the injector plug taken along line 5—5 of FIG. 4.

DETAILED DESCRIPTION OF THE INVENTION

In FIG. 1 the air-delivery and ventilation system of the present invention is generally described by reference numeral 10. The system 10 includes a flexible conduit 18 having discharge and inlet ends 19 and 21 respectively. The discharge end 19 is held in place over the chest of the patient by positioning bracket 20 and the inlet end of conduit 18 is connected to a rigid conduit 16, as shown in FIG. 2, through a connecting sleeve 15. Positioned in the right end of rigid conduit 16 is an injector plug 12, as shown in detail in FIGS. 4 and 5. Injector 12 includes a central passage 30 having a nozzle 32 in the end thereof for supplying a high-velocity jet of oxygen 50 along the center of conduit 18, as shown in FIG. 2. Central passage 30 is connected to a high pressure oxygen source, not shown in the drawing, through a flexible supply line 14. Injector plug 12 further includes three radial ribs 36 which position oxygen passage 30 in the center thereof and define three air inlet openings 34 which surround central passage 30, as best seen in FIG. 4. Surrounding the periphery of plug 12 is an outside diameter 54 which is frictionally received in the left end of rigid conduit 16, as seen in FIG. 2. Extending around the periphery of plug 12 is a flange 38 which limits insertion of plug 12 in conduit 16.

Positioning bracket 20 is formed of relatively thin-gauge aluminum or other bendable material and includes a pair of legs 42 connected by a saddle portion 44 which is partly circular in shaped, as seen in FIG. 3, for engagement of the conduit discharge end 19. The saddle 44 extends approximately 250° around discharge end 19 in spring-action contact therewith. Initially the pair of legs 42 are straight and lie adjacent each other until bent around the shoulders of the patient 23, as seen in FIG. 3. The height of the conduit 18 above the patient can be varied depending upon where the legs 42 are bent. The lower ends 46 of legs 42 are bent at right angles and inserted under the patient, between the operating table 26 and the pad 28, as shown in FIG. 3. The width 43 of the bracket 20, as seen in FIG. 2, is sufficiently wide so that when the ends 46 are tucked under the patient, the overall bracket has adequate longitudinal stability without any other stabilizing means.

OPERATION

With the patient 22 lying in place on operating table 26, the positioning bracket 20 is bent by the physician or attendant to achieve the desired height of the flexible conduit 18 above the chest of the patient. As the legs 42 are bent around the patient's body, the inside diameter of saddle 44 has a tendency to reduce its diameter and more tightly grip the discharge end 19 of the flexible conduit. The inlet end 21 of the flexible conduit is placed remotely in the vicinity of the feet of the patient so as not to draw in air with high concentrations of $CO_2$. The area of surgery on the patient is illustrated by dotted lines 52. The flow rate of pressurized oxygen is adjusted so that nozzle 32 admits a high velocity stream generating between 5 and 8 liters per minute. With the central oxygen passage 30 lying along the axis of conduit 16, the inlet air, which is drawn through openings 34, is flowing in an essential axial direction with a minimal amount of turbulence. The high-velocity jet 50 spreads outwardly as the high-velocity particles mix with the surrounding stationary air and move the entire air mass towards the discharge end 19 of the flexible duct. The volume of air exiting discharge end 19 is approximately 10 times the volume of oxygen introduced through the high speed jet 50. This exiting volume of oxygen-enhanced air (50 liters per minute) far exceeds the amount the patient breathes thereby washing away any $CO_2$ concentrations while providing a light breeze across the patient's face to inhibit claustrophobia and acute anxiety.

Whereas the present invention has been described with respect to specific embodiments thereof, it will be understood that various changes and modifications will be suggested to one skilled in the art and it is intended to encompass such changes and modifications as fall within the scope of the appended claims.

We claim:

1. An air delivery and ventilation system for head surgery used under a surgical drape comprising:
   a source of pressurized oxygen;
   a flexible air supply conduit with discharge and inlet ends;
   a positioning bracket means for positioning and holding the discharge end of the supply duct over the patient's chest, the bracket means being formed of bendable relatively thin-gauge metal shaped with a pair of legs joined by a partially circular saddle portion, the bracket means is positioned by bending each leg around the opposite shoulder of the patient;
   an injector means positioned in the inlet end of the flexible conduit, including a plug having a small diameter oxygen passage with a nozzle means in the discharge end thereof positioned in the center of the plug along the axis of the conduit and connected to the source of pressurized oxygen to produce a high velocity jet along the axis of the supply conduit; and
   at least one air passage means in the plug surrounding the oxygen passage for providing substantial volumes of atmospheric air drawn into the conduit by the venturi action of said high velocity jet which provides low velocity oxygen-enhanced air from the discharge end of the air supply conduit.

2. An air delivery and ventilation system as set forth in claim 1, herein the legs of the bendable bracket have a width approximate the diameter of the supply conduit to give the bracket longitudinal stability when in place with the legs inserted under the patient.

3. An air delivery and ventilation system as set forth in claim 1 wherein the plug includes a plurality of radially spaced ribs which position the oxygen passage in the center of the plug.

4. An air delivery and ventilation system as set forth in claim 1 wherein the plug includes a plurality of radially spaced ribs which position the oxygen passage in the center of the plug, the ribs defining at least two separate air passage means having a combined cross-sectional area substantially greater than the cross-sectional area of the oxygen passage.

5. An air delivery and ventilation system as set forth in claim 1, wherein the inlet end of the air supply conduit is remotely positioned from the discharge end outside the surgical drape so that high density $CO_2$ air is not drawn into the inlet ends.

* * * * *